(12) United States Patent
Makdissi

(10) Patent No.: US 8,963,737 B2
(45) Date of Patent: Feb. 24, 2015

(54) RF TELEMETRY RECEIVER CIRCUIT FOR ACTIVE MEDICAL IMPLANTS

(75) Inventor: Alaa Makdissi, Paris (FR)

(73) Assignee: Sorin CRM SAS, Clamart (FR)

(*) Notice: Subject to any disclaimer, the term of this patent is extended or adjusted under 35 U.S.C. 154(b) by 375 days.

(21) Appl. No.: 13/536,492

(22) Filed: Jun. 28, 2012

(65) Prior Publication Data

US 2013/0002448 A1 Jan. 3, 2013

(30) Foreign Application Priority Data

Jun. 28, 2011 (FR) ...................... 11/55759

(51) Int. Cl.
*G08C 19/16* (2006.01)
*H04B 1/22* (2006.01)
*A61N 1/372* (2006.01)

(52) U.S. Cl.
CPC .............. *H04B 1/22* (2013.01); *A61N 1/37276* (2013.01); *A61N 1/3727* (2013.01)
USPC .......... 340/870.4; 333/133; 333/188; 607/32; 607/60

(58) Field of Classification Search
USPC ............. 340/870.4, 870.41, 870.15; 333/133, 333/188, 189, 190; 607/32, 60
See application file for complete search history.

(56) References Cited

U.S. PATENT DOCUMENTS

| 5,929,779 A | 7/1999 | MacLellan et al. |
| 6,453,200 B1 | 9/2002 | Koslar |
| 7,663,451 B2 | 2/2010 | Dal Molin |

FOREIGN PATENT DOCUMENTS

| DE | 4440113 A1 | 5/1996 |
| DE | 19646746 A1 | 5/1998 |
| DE | 10209855 A1 | 9/2003 |
| EP | 1862195 A1 | 12/2007 |

OTHER PUBLICATIONS

Foreign Search Report (Annexe Au Rapport De Recherche Preliminaire Relatif a La Demande De Brevet Francais No. FR 1155759 FA 755819), Mar. 13, 2012.

*Primary Examiner* — Nabil Syed
(74) *Attorney, Agent, or Firm* — Foley & Lardner LLP

(57) ABSTRACT

An RF telemetry receiver circuit for active implantable medical devices. The baseband binary signal ($D_b$) is doubly modulated by a low frequency carrier ($F_m$) and by a high frequency carrier ($F_c$). The receiver circuit is a semi-passive non heterodyne circuit, devoid of a local oscillator and mixer. It comprises an antenna (104), a passive bandpass filter (108) centered on the high-frequency carrier ($F_c$), a passive envelope detector (120-126) and a, digital demodulator (116). The envelope detector comprises a first diode circuit (120) of non-coherent detection, an active bandpass filter (122) centered on a frequency ($2.F_m$) twice the low frequency carrier and having a bandwidth ($2.D_b$) twice the baseband bandwidth, and a second diode circuit (124) of non-coherent detection, outputting a baseband signal applied to the digital demodulation stage (116).

7 Claims, 3 Drawing Sheets

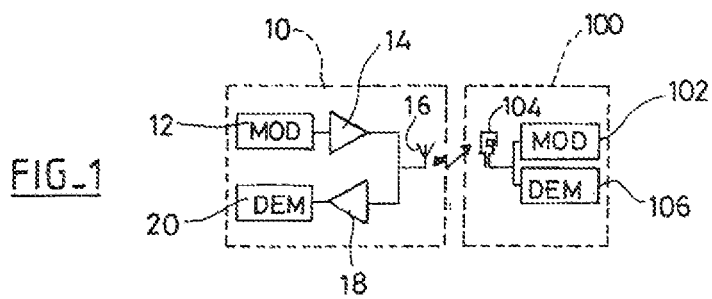
FIG_1
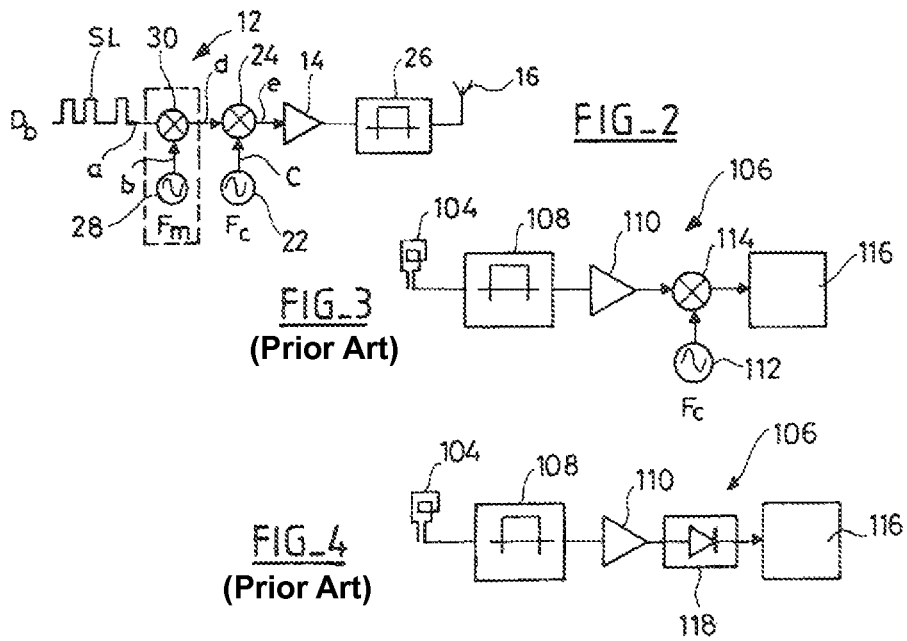
FIG_2
FIG_3 (Prior Art)
FIG_4 (Prior Art)
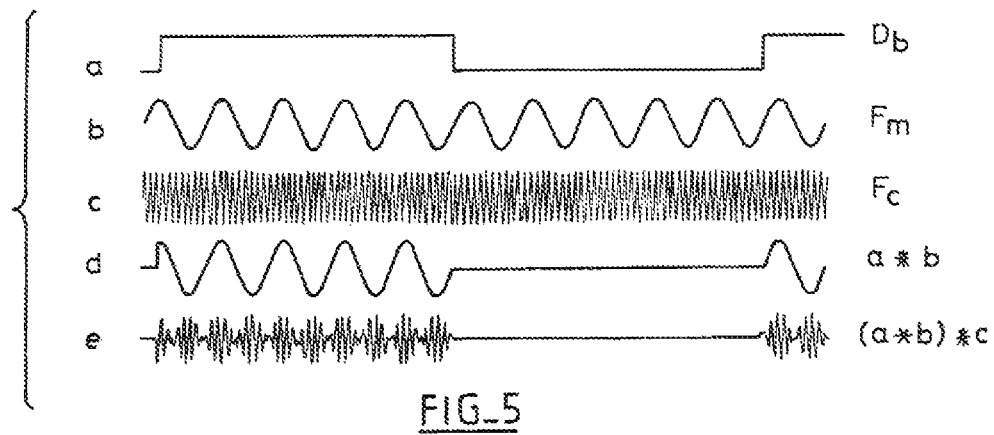
FIG_5

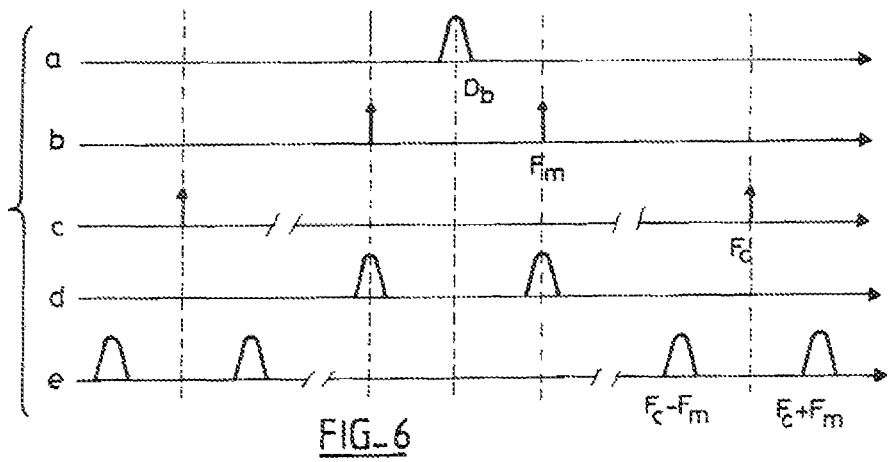
FIG_6
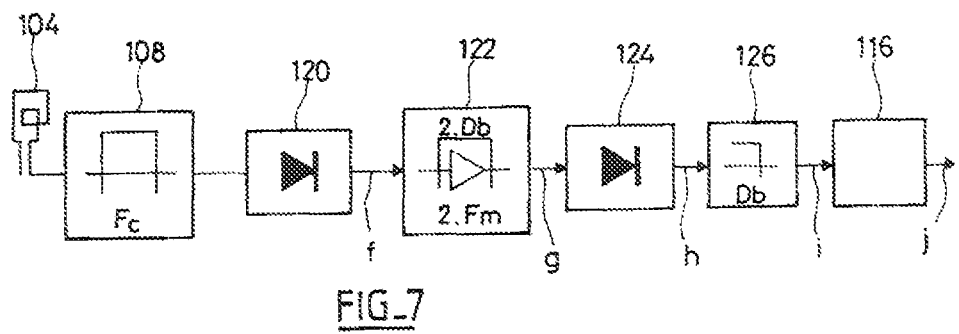
FIG_7
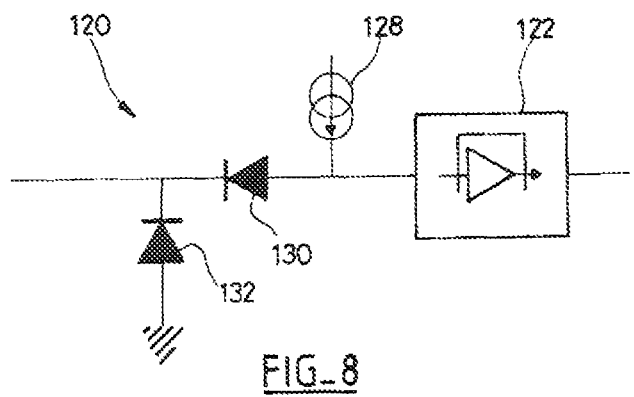
FIG_8

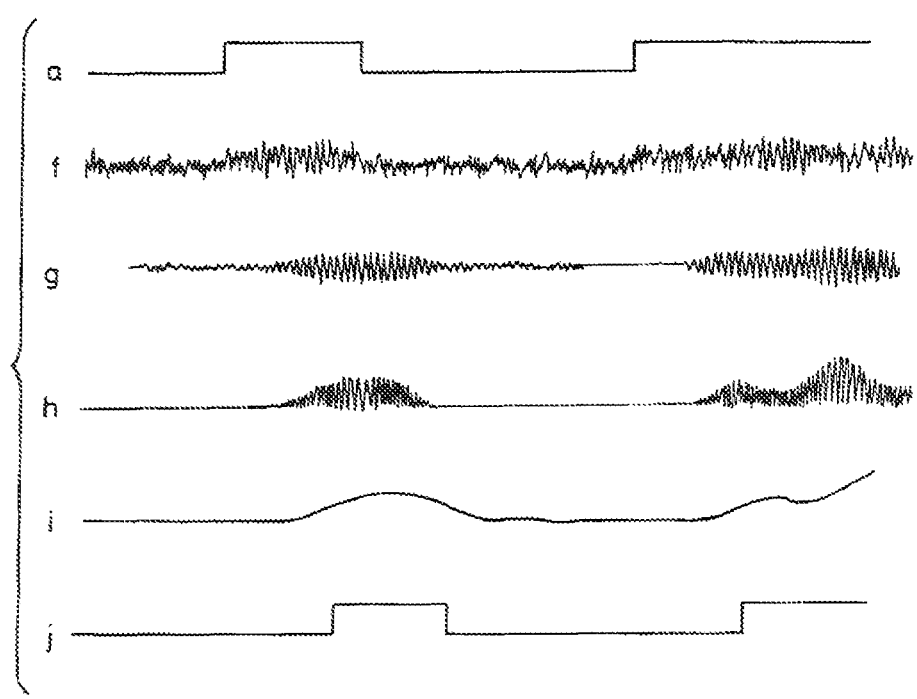
FIG_9

RF TELEMETRY RECEIVER CIRCUIT FOR ACTIVE MEDICAL IMPLANTS

RELATED APPLICATIONS

The present application claims the priority date benefit of French Application No. 11/55759 entitled "RF telemetry receiver circuit for active medical implants" and filed Jun. 28, 2011, which is hereby incorporated by reference in its entirety.

FIELD

The present invention relates to "medical devices" as defined by the Jun., 14, 1993 Directive 93/42/CE of the European Community Council, and more particularly to "active implantable medical devices" as defined by the Jun. 20, 1990 Directive 90/395/CEE of the European Community Council. Such devices include in particular apparatus responsible for monitoring cardiac activity and generating stimulation pulses for resynchronization, defibrillation and/or cardioversion, in case of an arrhythmia detected by the device. It also includes neurological devices, pumps for the diffusion of medical substances, cochlear implants, implanted biological sensors, etc., and devices for measuring pH or intracorporeal impedance (such as transpulmonary impedance or intracardiac impedance). It should be understood that the present invention is particularly advantageous with implanted devices such as pacemakers, cardioverters or defibrillators, and equally with non-implanted medical devices, such as data recorders like external Holter devices intended for ambulatory patient monitoring and recording of physiological parameters such as cardiac activity.

BACKGROUND

Active medical devices are generally designed to enable a bidirectional data exchange with a remote "programmer," which is an external device, for a variety of reasons, e.g., to verify the configuration of the device, to read information the device has recorded, to post information to the device, or to update the internal software of the device.

Techniques for monitoring patients at home (home monitoring) have been proposed that implement a remote interrogation device disposed adjacent to the implanted patient, which is periodically activated, e.g., daily, to download data collected by an implanted device and transmission for analysis to a remote surveillance site. Data exchange between an implantable device and the programmer or home monitoring device (hereinafter, collectively an "external device") is generally performed by telemetry, that is to say, by a communication technique for remote transmission of information, without galvanic contact.

A common telemetry technique uses inductive coupling between coils located inside the implanted device and those in the external device, which technique is known as "induction telemetry". The induction telemetry technique has the disadvantage, because of the very limited range of such a coupling, to require the use of a "telemetry head" connected to the external device and containing a coil that an operator places in the vicinity of the site in which the device is implanted.

It was recently proposed to implement an alternative technique for non-galvanic coupling, using an electromagnetic wave generated by and between complementary transmitter/receiver circuits operating in the radiofrequency (RF) domain, typically in the range of frequencies of several hundred megahertz. This technique, known as "RF telemetry" allows programming or interrogating implants at distances greater than 3 m, and therefore permits the exchange of information without manipulation of a telemetry head, and indeed even without external operator intervention.

An active medical device implementing RF telemetry is described for example in EP1862195A1 and its US counterpart U.S. Pat. No. 7,663,451 (both assigned to Sorin CRM S.A.S., previously known as ELA Medical).

Power Consumption by RF telemetary circuits is a crucial aspect of this RF technique, especially with regard to an implanted device. Indeed, the implanted devices use for energy sources a battery whose energy capacity is limited (about 1 Ah). Without RF telemetry, the average consumption of an implanted device is about 20 μW, which provides autonomy (i.e., a useful life under normal circumstances) of about a dozen years. However, upon activation of a RF telemetry function, an implanted device typically consumes, with current technologies, a dozen milliwatts, about 500 to 1000 times more than its average consumption for the usual functions of cardiac sensing and pacing.

On the other hand, it is known that the environment surrounding the patient has more and more radio frequency interferences that could inadvertently and adversely wake up the RF telemetry circuit of the implanted device and therefore unnecessarily discharge the battery of the implanted device.

Occasional use of the RF telemetry once every three or six months, for example, in connection with follow-up visits to the cardiologist, does not significantly degrade the autonomy of the implanted device. However, daily use to communicate with a home monitoring device can significantly reduce the lifetime of the implanted device. Indeed, if for example a quarter of the capacity of the battery is assigned to the RF telemetry functions, this capacity provides only 50 hours of continuous RF communication throughout the useful life of the implanted device (10 years), or a daily use of less than 50 seconds.

Knowing that the current RF telemetry systems use communication channels of bandwidth limited to 300 kHz with a data rate of about 100-200 kbps (kilobits per second), and that the electrogram ("EGM") signals are sampled on 10 bits and 500 times per second, a transmission duration of 50 seconds per day allows transmission to the external device (taking into account the overload introduced by the communication protocol) of only a maximum of 8 minutes recording of two EGM signal channels.

There is therefore a need for an intensive use of a remote RF telemetry system that is efficient in terms of energy use without penalizing the autonomy of the implanted device.

OBJECT AND SUMMARY

The starting point of the present invention lies in the implementation in the implanted device of communication circuits whose power consumption and complexity are minimal, even at the expense of increasing the complexity of circuits and power consumption of the external devices. Indeed, the latter operates with a not limited power source available from a commercial line service or a battery of a much larger capacity than the battery of an implanted device and are also easily replaceable or rechargeable.

In accordance with the present invention, the RF signals originating from the external device are chosen with a modulation structure to make the reception circuit in the implanted device as simple as possible and of very low power consumption, such that the complexity and the additional consumption to generate this specific RF signal modulation is managed by the external device.

Broadly, the present invention is directed to an RF telemetry reception circuit that is in itself known, for example, according to the document DE 196 46 746 A1 and its counterpart U.S. Pat. No. 6,453,200 B1, which is incorporated herein by reference, for active medical implantable devices, an RF signal which has a binary signal at a baseband data rate that contains the information to be transmitted, which undergoes a double-modulation for the transmission by RF telemetry, in which the binary base band signal undergoes a first modulation by a first carrier frequency to produce a first modulated signal, and that first modulated signal is then subjected to a second modulation by a second carrier frequency, thereby provided the double modulated signal to be transmitted. The first carrier frequency is a lower frequency carrier than the second carrier frequency.

The reception circuit successively comprising: an antenna for reception of an RF signal, here the double modulated RF signal; a band-pass filtering and impedance matching stage that operates on the received RF signal captured by the antenna; a envelope detector stage that receives and operates on the filtered signal delivered by the front filtering stage and performs a first demodulation of the received and filtered RF signal, and a digital demodulation stage that receives and operates on the first demodulated RF signal delivered by the envelope detector stage and produces the binary signal at the base band containing the information to be transmitted.

The front filtering stage is centered on the frequency of the second or high-frequency carrier. The envelope detector stage is a non heterodyne detection stage, without any local oscillator or mixer, and comprises: a first non-coherent detection diode circuit, receiving as input the filtered signal delivered by the upstream filtering stage; an active bandpass filter, receiving as input the signal delivered by the first non-coherent detection diode circuit, this active band-pass filter being centered on a frequency twice that of the first or low frequency carrier and having a frequency bandwidth that is twice that of the base band, and a second diode non-coherent detection circuit, receiving as input the signal delivered by the active bandpass filter and outputting a baseband signal applied to the digital demodulation stage.

Most advantageously, the optimization also focuses on the choice of the frequency bands used for transmission of RF signals. Moreover, both regarding the modulation mode and the available channels in the selected frequency band, the present invention implements a non-symmetrical configuration between the two communication directions (a "Downlink" configuration from the external device to the implanted devices and "Uplink" configuration from the implanted device to the external device).

The present invention also advantageously results in the Downlink configuration reducing the consumption of the RF telemetry system by one to two orders of magnitude (a improvement factor of from ×10 to ×100) compared to prior known. RF telemetry systems, thus maintaining a very long autonomy of the implanted device even with intensive use of the RF telemetry information exchange.

The present invention advantageously results in a modulation structure of the RF signal transmitted from the external device to the implanted device, whereby the Downlink configuration direction can greatly reduce RF interference, thereby avoiding degradation of energy consumption and therefore the autonomy of the implanted device by an inadvertent or adverse wake up of the RF telemetry reception circuit.

In one embodiment, the reception circuit of the present invention is a "semi-passive" circuit, meaning that the components that are energy consumers are reduced to a minimum number. In particular, this circuit neither includes a local oscillator or a mixer, unlike conventional heterodyne demodulator reception circuits. The reception circuit can even be devoid of a Low Noise Amplifier ("LNA").

More particularly, this reception circuit is not only "semi-passive" but also particularly selective, making it usable in particular frequency bands shared by many users, allowing the choice of a band that may be more appropriate than that usually devoted to the RF transmission in the field of medical implanted devices.

In one embodiment, the first diode non-coherent detection circuit comprises a diode bias current source:

In one embodiment, the first diode non-coherent detection circuit comprises a two diode detector configured as a voltage doubler.

In one embodiment, the frequency of the high-frequency carrier is in the 2.4 GHz ISM band or in the 900 MHz RFID band.

In one embodiment, the frequency of the low frequency carrier is between 25 and 500 kHz.

In one embodiment, the frequency of the baseband signal is between 5 and 100 kbps.

In one embodiment, the gain of the active bandpass filter is between 30 and 50 dB.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 is a schematic view of the functional blocks involved in the RF telemetry data exchange for an implanted device and an external device in accordance with the present invention;

FIG. 2 is a schematic representation of the main functional blocks of the emission portion of the external device of FIG. 1.

FIG. 3 schematically illustrates the main functions implemented in a heterodyne reception circuit of the prior art;

FIG. 4 schematically illustrates the main functions implemented in a Schottky diode non-coherent detection reception circuit according to the prior art;

FIG. 5 shows a series of signal timing diagrams in various parts of the external device transmitter circuit shown in FIG. 3;

FIG. 6 is homologous to FIG. 5, showing the distribution of the various signals in question, considered in the frequency domain;

FIG. 7 schematically illustrates the main functions implemented by the semi-passive reception circuit of the implanted device of FIG. 1, according to the present invention;

FIG. 8 shows a variant of the circuit of FIG. 7, with bias current and voltage doubler; and FIG. 9 shows a series of timing diagrams of signals recorded at various points in the reception circuit of FIG. 7.

DETAILED DESCRIPTION

With reference to the drawing FIGS. 1-9, an implementation of the present invention in accordance with preferred embodiments will now be described. With reference to FIG. 1 the circuits of an RF emission/reception system of an external device 10 communicating with an implanted device 100 are schematically illustrated. External device 10 is equipped with a modulator ("MOD") 12 delivering a signal to a power amplifier 14 powering an emission antenna 16. For the reception part inside the external device, the signals collected by the antenna 16 are amplified by a low noise amplifier (LNA) 18 powering a demodulator ("DEM") 20.

Implanted device 100 comprises a modulator circuit (MOD) 102 powering an antenna 104 for data transmission to external device 10 (i.e, an RF transmission in the uplink direction). In the downlink direction (i.e., the direction from external device 10 to implanted device 100), a demodulator (DEM) 106 collects the signals received by antenna 104 of implanted device 100.

The RF telemetry data exchange between external device 10 and implanted device 100 may be asymmetrical. More specifically:
  The modulation types are not the same in both directions (that is to say that modulators 12 and 102 do not operate using the same modulation technique, and therefor as well demodulators 20 and 106, consequently), and
  In the selected frequency band, different channels can be used in one direction and in the other.

With reference to FIG. 2, modulation stage 12 of the external device 10 is illustrated. It includes a local oscillator 22 the frequency $F_c$ of which is applied to a mixer 24 also receiving the digital signal to be transmitted (logic signal SL). The resulting signal, after passing through power amplifier 14 is applied to antenna 16 via a selective bandpass filter 26 to limit the residual spectrum of the signal outside the considered transmission band.

FIG. 3 schematically illustrates the main functions implemented in a heterodyne reception circuit according to the state of the art, for the reception and the demodulation of the signal emitted by the external device 10.

In such a conventional receiver (Cf. the Wikipedia article "Récepteur radio"), the signal collected by antenna 104 is applied to an impedance matching and band-pass filtering circuit 108, to maximize the signal/noise ratio at the input of the reception circuit. The resulting signal is applied to a low noise amplifier (LNA) 110 which amplifies the received signal in the frequency band of the carrier $F_c$. The demodulation is carried out by a local oscillator 112, the frequency of which is $F_c$ and a mixer 114 receiving the filtered received signal. The baseband signal obtained by frequency translation is then applied to a digital demodulation stage 116 to restore the output logic signal transmitted from the original external device.

It should be understood that this conventional structure of the reception circuit includes amplifier 110, local oscillator 112 and mixer 114 as active circuits, which can represent up to 90% of the overall consumption of the reception circuit (the digital demodulation stage 116, which operates at low frequency, has a relatively low power consumption).

FIG. 4 shows an alternative reception circuit, also of the prior art (Cf. for example U.S. Pat. No. 5,929,779 A, FIG. 3), having no local oscillator and no mixer stage. These elements are replaced by a diode 118 for non-coherent detection, for example, a Schottky diode, which is a passive component. The main active component of this embodiment is an energy amplifier 110, which leads to consumption two to three times less than that of the conventional heterodyne detection circuit of FIG. 3. This reception circuit has a drawback due to the fact that the diode detector 118 operates according to a quadratic voltage conversion of the amplified RF signal. It can be shown that such a receiver is therefore a non-selective receiver, which therefore simultaneously senses all present RF signals in the communication band defined by filter 108. This lack of selectivity makes this type of receiver unusable in frequency bands shared by many users. It is certainly possible to improve their selectivity by very narrow band filters, but they are difficult to implement in an implanted device because of their large size.

In any event, even if such a receiver is tuned on a single channel of communication to eliminate interference from other channels of the same band of communication, the energy consumption of the amplifier 110 remains high (a few milliwatts) because it operates in High Frequency and does not allow extensive use of this receiver in a cardiac implanted device whose permanent consumption is, as noted above, only a few tens of microwatts.

The technique used by the present invention to overcome these various disadvantages of the prior art will now be described.

The present invention uses a double modulation of the signal in the downlink direction (from the external device to the implanted device), and the external device is adapted accordingly. More precisely, with reference to FIG. 2 described above, in addition to the modulation by the main carrier at frequency $F_c$ (oscillator 22 and mixer 24), a prior modulation of the signal is expected by a lower frequency $F_m$, by another local oscillator 28 associated with another mixer 30.

FIG. 5 illustrates the timing diagrams of the signals recorded at different points a to e of the modulation circuit of the external device of FIG. 2. The timing diagram a illustrates the logic signal SL containing information to be transmitted. This signal is produced at a digital rate $D_b$ (baseband signal) on the order of 5 to 100 kbps. One can for example use a NRZ (non return to zero) modulation in which the binary ones are represented by a logic signal of given amplitude V, and logic zeros by zero amplitude.

This signal a in the baseband is subjected to a double modulation, respectively by the $F_m$ low frequency carrier signals and then by high frequency carrier signals $F_c$. It is specified here that the terms "low frequency" and "high frequency" are relative terms (the two frequencies are different, and one is higher than the other) and do not imply any particular connotation on the chosen value, in absolute terms for each of these frequencies. The numerical values that are given should be considered only as illustrative values, without limitation.

The low frequency carrier $F_m$ (signal b) is advantageously at a frequency of the order of five to ten times the frequency of the baseband Db, that is to say a frequency between 25 and 500 kHz.

The high frequency carrier $F_c$ (signal c) corresponds to the selected RF band, which is advantageously the 2.4 GHz band (more precisely, the band between 2.40 and 2.45 GHz), which is the unlicensed public ISM band (Industrial, Scientific and Medical). It could also be any authorized "RFID" band in the MHz range.

This 2.4 GHz ISM band is indeed preferred to the MICS band (Medical Implant Communication System) 402-405 MHz generally used by medical devices, for the following reasons. In the 2.4 GHz band, an RF signal transmitted from an external device located two meters from the patient to an implanted device located a few centimeters under the patient's skin is attenuated in the order of 70-80 dB. In the MICS band, the maximum permissible power is only −16 dBm (25 mW). However, in the ISM band, the maximum permitted power is 20 dBm (100 mW), and can reach 30 dBm (1 W) if one uses digital modulation techniques such as Frequency Hopping. It is thus possible to have a much higher power—on the order of 1000 to 10 000 times higher (30 to 40 dB)—and so obtain more power into the implanted device, with a lesser signal amplification. Thus, for a signal whose emitted RF power is between 10 dBm and 30 dBm (10 mW to 1 W) and an attenuation of 70 to 80 dB, the power of the RF signal received by the implanted device, before amplification, is comprised between −40 dBm and −70 dBm (100 mW and 100 pW).

The timing diagram d represents the logic signal after modulation by the low frequency carrier (product of signals a and b), and the timing signal e represents the same signal after the second modulation by the high-frequency carrier $F_c$ (product of signals d and c).

FIG. 6 shows the distribution of the different signals a to a in the frequency domain. The spectrum of the signal a is that of the baseband binary signal $D_b$, centered around the zero frequency, and occupies the frequency band between −$D_b$ and +$D_b$. The spectrum of the signal b is that of the low frequency carrier, and includes a peak at the frequency +$F_m$ and a peak at the frequency −$F_m$. The spectrum of the signal c is that of the high frequency carrier, and includes a peak at the frequency +$F_c$ and a peak at the frequency −$F_c$. The spectrum of the signal d (after the first modulation) comprises the spectrum of the baseband signal a, centered on the frequency +$F_m$. The occupied bandwidth is 2 $D_b$. Finally, the spectrum of the signal e (after the second modulation) contains twice the spectrum of the baseband signal, with a sub-band centered around $F_c$−$F_m$, and another around $F_c$+$F_m$, both sub-bands therefore being separated by 2.$F_m$.

The double modulation is certainly not spectrally efficient, because one can show that the spectrum of the transmitted signal occupies four times the bandwidth of the baseband binary signal. However, although this double modulation is not optimal from a spectral point of view, it can be seen later that it permits to realize a semi-passive selective receiver in the implanted device which is advantageous for other reasons.

This selectivity, very important to get a good quality receiver, exploits the fact that the two sub-bands of the spectrum of the transmitted signal (signal e) are always separated by 2.$F_m$ regardless of the frequency of the high frequency carrier $F_c$.

The semi-passive reception circuit of the implanted device, according to the present invention, will now be described with reference to FIGS. 7 and 9. This reception circuit is specifically adapted to utilize the double modulation technique as described above. The doubly modulated RF signal is received by antenna 104. This signal is applied to an impedance matching and passive bandpass filtering stage 108 centered on the frequency of the high-frequency carrier $F_c$ to attenuate signals outside the selected band. The signal thus filtered is then applied to a first non-coherent detection circuit 120, comprising a diode, preferably a Schottky diode, which performs the envelope detection by rectifying the signal according to a square (quadratic) equation.

The signal delivered by the first envelope detector 120 (signal f in FIG. 9) is then applied to a filter 122 which, typically, is an active bandpass filter centered around the 2.$F_m$ frequency, and having a bandwidth of the order of 2.$D_b$. Such an active filter 122 is easy to implement in standard CMOS technology, which consumes little energy. Filter 122 has a gain high enough to make detection of the signal in the following stages of the reception circuit feasible. Preferably, it is possible to produce such an active filter 122 with a voltage gain of 100 (40 dB) with a consumption of about 10 µA.

It should be understood that the double modulation (low frequency carrier and high-frequency carrier) used by the circuit of the present invention overcomes the limitations of a conventional non-coherent detection circuit with diode of the prior art such as the one shown in FIG. 4. Indeed, in such a detector operating on a single carrier frequency, we get only at the output of the detection stage a DC component and this is for all frequencies within the useful band, that is to say the band selected by the upstream filter 108. This DC component is very noisy and corrupted, resulting in a poor transmission quality of the digital signal from the external device to the implant.

The double modulation used by the present invention, however, allows a much more robust transmission because, due to the double modulation, detection by diode 120 generates at its output not a DC component, but instead a signal corresponding to the frequency of bandpass filter 122. Thus, the downstream signal processing for extracting the digital information is made on the basis of the component located around the frequency 2.$F_m$, and not on a noisy and corrupted DC component.

It also should be understood that the signal f at the output of the first envelope detector circuit 120 after filtering of the high frequency component by filter 108 has a signal/noise ratio of +5 dB, well below the tangential sensitivity of +8 dB of the diode of circuit 120. Indeed, although the signals at the output from a diode detector are very small, the noise level in these very weak signals determines the receiver sensitivity. In this case, in view of the double modulation of the signal, it is possible to detect a very low signal level at the output of diode detector 120. The sensitivity of this detector can be characterized by the tangential sensitivity parameter ("TSS") of the signal, which is defined as the signal level which gives a signal/noise ratio equal to 8 dB at the output of the detector.

This tangential sensitivity is related to the bandwidth of the amplifier stage located after (and not before) of the detector according to the equation TSS=K√B, K being a constant and B being the bandwidth at the output. This relationship shows that the sensitivity of the diode receiver can be greatly improved by reducing the bandwidth of the filter located at the output of the detector, i.e. by increasing the integration time of the output signal.

In accordance with a preferred embodiment of the invention, the amplifier of active filter 122 has a bandwidth B=2.$D_b$, as indicated above. The constant K between the bandwidth B and the TSS is on the order of $1.4 \times 10^{-12}$ in the diode detector of the HSMS-285X family of Avago Technologies, Inc. For a data rate of 5 kbps, this bandwidth is 10 kHz, a TSS sensitivity of −68.5 dBm; for a data rate of 100 kbps, the TSS is equal to −62 dBm.

The timing diagram g of FIG. 9 shows the signal obtained at output of active bandpass filter 122. This signal is applied to a second diode envelope detector circuit 124 outputting a signal (h in FIG. 9) corresponding to the absolute (or rectified) value of the inputted signal g. This circuit is followed by a low-pass filter 126 fitted to a cutoff frequency corresponding to the baseband frequency $D_b$. The resulting signal is illustrated in i in FIG. 9.

The latter signal is applied to a digital demodulation stage 116, for example constituted by a hysteresis comparator combined with a counter, which retrieves at the output (signal j) the original signal delivered by the external device (signal a) with simply a time offset corresponding to the integration time of the circuits. The counter can be operated with a low-power clock at low frequency, of the order of 5.$D_b$ that is to say of the order of 25 to 500 kHz. Consumption of such a digital demodulation circuit 116 may be less than 1 µA.

It should be understood that the reception circuit according to the present invention as described above does not contain any active circuit operating in the frequency band of the high-frequency carrier $F_c$, thus limiting the consumption of the reception circuit.

The total consumption of the reception circuit illustrated in FIG. 7 may thus be well below 15 μA, which is about 100 to 500 times less than the best heterodyne receivers available today.

As regards the sensitivity of the receiving circuit, it is essentially a function of signal/noise ratio at the stage containing the first envelope detector 120.

It is generally believed that the sensitivity of a receiver for non-coherent detection (such as that shown in FIG. 4) is much lower than that of a heterodyne receiver (such as that shown in FIG. 3): thus, the non coherent envelope detection receivers of in the ISM band 2.4 MHz generally have sensitivity between −40 and −50 dBm.

This would suggest that such an assembly would be difficult to use in an implanted device, wherein the power of received signals typically varies between −40 and −70 dBm, depending on the emission power. The circuit of the present invention, however, operates precisely contrary to this generally accepted idea.

It is possible to further improve the sensitivity of the reception circuit as described above. In particular, in a preferred embodiment, providing a high input impedance for the amplifier stage of active bandpass filter 122 improves sensitivity and allows the use of a low-frequency carrier at a relatively low $F_m$ frequency.

Another method to improve sensitivity by reducing consumption is to use for stage 120 two diodes 130, 132 connected in a voltage doubler, as shown in FIG. 8. The use of two diodes to double the voltage increases the level of the input signal of active filter 122, and thereby reduces the gain of this amplifier, with a corresponding reduction in power consumption.

Yet another method to increase the sensitivity is, as shown also in FIG. 8, to inject into the diode(s) a bias current on the order of 100 nA to 10 μA by means of a current generator 128. The value of this bias current is chosen to maximize sensitivity depending on the characteristics of the diode used, taking particular account of the fact that the tangential sensitivity TSS is not linear. Bias current, fixed or variable as a function of the received power, thus optimizes the conversion gain energy/voltage of the diode(s).

Compared with a circuit such as that shown in FIG. 7 without bias current and with a single diode, the circuit configuration illustrated in FIG. 8 provides a gain of 6 dB and a sensitivity of about −75 dBm for a data rate $D_b$ of 5 kbps. Despite this sensitivity of −75 dBm being less than that obtained with a heterodyne receiver (on the order of −100 dBm for a data rate of 100 kbps), it is largely sufficient to obtain a very good receiver for low signal data rates. Indeed, in the downlink direction (from the external device to the implanted device) the volume of information to be transmitted is relatively limited, since it mainly consists of commands and parameters sent to the implant—unlike the uplink direction, wherein a large amount of data stored in the memory has to be downloaded from the implanted device, such as EGM data collected over a period of 24 hours or even days.

Moreover, in terms of energy consumption, the 10 mW consumption of a conventional heterodyne receiver for a data rate of 200 kbps leads to a cost of 50 nJ/bit, while the receiver of the present invention consumes less than 50 μW for a data rate of 100 kbps, an energy cost of 0.5 nJ/bit, a hundred times less.

In addition to reducing consumption, simplicity of construction of the reception circuit (essentially, two diode detectors and a low frequency selective amplifier) allows a very simple hardware implementation, without any active component operating in the band of RF frequencies.

Yet another advantage of the receiver according to the present invention is its ability to take into account a signal whose RF carrier frequency (the high frequency carrier $F_c$) varies in time, for example, in case of modulation with frequency hopping to secure the reception circuit onto search among several possible channels one that is less noisy and/or provides the best transmission: indeed, the first envelope detection circuit 120 is insensitive to the carrier frequency $F_c$, so that there is no need to adjust any communication channel on the receiver side.

One skilled in the art will appreciate that the present invention can be practiced by other embodiments other than those described herein, which are provided for purposes of illustration and explanation, and not of limitation.

The invention claimed is:

1. An RF telemetry reception circuit for an active implantable medical device, comprising:

n antenna (104) for receiving a double-modulation RF signal waveform, said double-modulation RF signal comprising a binary signal (a) in a baseband with a bandwidth ($D_b$) that has a first modulation by a first carrier frequency (b), to give a first modulated signal (d), and the first modulated signal (d) has a second modulation by a second carrier frequency (c), the first carrier frequency being a lower frequency ($F_m$) than the second carrier frequency ($F_c$)

an input stage (108) having an input corresponding to said received RF signal and a bandpass filter having a bandpass centered on the second carrier frequency ($F_c$), an impedance matching circuit, and an output, said output being a filtered RF signal;

an envelope detector stage that is a non heterodyne detection stage, with no local oscillator and no mixer, and comprises:

a first diode circuit (120) of non-coherent detection, receiving as an input the filtered RF signal;

an active bandpass filter (122), receiving as an input the signal (f) delivered by the first non-coherent detection diode circuit, this active bandpass filter having a band pass centered on a frequency ($2.F_m$) that is twice that of the first frequency carrier ($F_m$) and having a bandwidth ($2.D_b$) twice that of the baseband ($D_b$), and a second diode circuit (124) of non-coherent detection, receiving as input the signal (g) delivered by the active bandpass filter and outputting a baseband signal (h), and a digital demodulation stage (116) having an input corresponding to the baseband signal and an output corresponding to said binary signal of said received RF signal.

2. The receiver circuit of claim 1, wherein the first diode non-coherent detection circuit further comprises a current source (128) for diode bias.

3. The receiver circuit of claim 1, wherein the first diode non-coherent detection circuit further comprises a diode detector having two diodes (130, 132) configured as a voltage doubler.

4. The receiver circuit of claim 1, wherein the second carrier frequency ($F_c$) is in one of the 2.4 GHz ISM band and the 900 MHz RFID band.

5. The receiver circuit of claim 1, wherein the first carrier frequency ($F_m$) is between 25 and 500 kHz.

6. The receiver circuit of claim 1, wherein the baseband signal (Db) has a data rate of between 5 and 100 kbps.

7. The receiver circuit of claim 1, wherein the bandpass filter further comprises (122) a gain of between 30 and 50 dB.

* * * * *